(12) United States Patent
Hernández et al.

(10) Patent No.: US 8,579,503 B2
(45) Date of Patent: Nov. 12, 2013

(54) DEVICE TO CONTINUOUSLY DETERMINE THE RATE OF EXTRACTION OF WATER STEAM USED FOR DRYING TRANSFORMERS

(75) Inventors: David Diguero Hernández, San Pedro Garza García (MX); Manuel Antonio Cano Urrego, Bogotá (CO)

(73) Assignee: Prolec Ge Internacional, S. de R.L. de C.V., Apodaca, Nuevo Leon ( * ) Notice: Subject to any disclaimer, the term of this patent is extended or adjusted under 35 U.S.C. 154(b) by 18 days.

(21) Appl. No.: 13/226,574

(22) Filed: Sep. 7, 2011

(65) Prior Publication Data

US 2013/0058375 A1    Mar. 7, 2013

(51) Int. Cl.
*G01N 17/00* (2006.01)
*G01N 7/00* (2006.01)
*G01N 19/10* (2006.01)

(52) U.S. Cl.
USPC .............................. 374/24; 73/29.01; 73/29.02

(58) Field of Classification Search
USPC ............................................. 73/29.01, 29.02
See application file for complete search history.

(56) References Cited

U.S. PATENT DOCUMENTS

| | | | | |
|---|---|---|---|---|
| 4,131,011 | A * | 12/1978 | Ling | 73/29.01 |
| 5,331,747 | A * | 7/1994 | Stanton | 34/405 |
| 5,556,607 | A * | 9/1996 | Childers et al. | 422/300 |
| 5,663,491 | A * | 9/1997 | Beer | 73/61.41 |
| 6,550,324 | B1 | 4/2003 | Mayer et al. | |
| 6,804,970 | B2 * | 10/2004 | Saeki et al. | 62/133 |
| 6,894,761 | B2 * | 5/2005 | Ayash et al. | 355/30 |
| 7,332,013 | B2 * | 2/2008 | Arno et al. | 55/518 |
| 7,395,673 | B2 * | 7/2008 | Mitter | 62/176.1 |
| 7,500,349 | B2 * | 3/2009 | Althaus | 60/39.511 |
| 7,516,651 | B2 | 4/2009 | Aubin et al. | |
| 7,565,808 | B2 * | 7/2009 | Sullivan | 62/5 |
| 7,628,058 | B2 * | 12/2009 | Legrand | 73/64.55 |
| 2004/0159146 | A1 | 8/2004 | Belanger | |
| 2008/0177242 | A1 * | 7/2008 | Chang et al. | 604/385.01 |
| 2010/0288016 | A1 * | 11/2010 | Basar | 73/29.02 |

OTHER PUBLICATIONS

Savage M. "Field Evaluation of Polymer Capacitive Humidity Sensors for Bowen Ratio Energy Balance Flux Measurements", Senso, vol. 10, pp. 7748-7771.*

* cited by examiner

*Primary Examiner* — Lisa Caputo
*Assistant Examiner* — Nasir U Ahmed
(74) *Attorney, Agent, or Firm* — Miller, Matthias & Hull LLP

(57) ABSTRACT

A moisture flow meter is provided in the air at negative pressures in the drying of transformers by means of a vacuum process for water extraction, causing a differential of pressure through a device of orifice plate and the continuous measurement of the dewpoint. The meter includes a pipeline, a continuous dewpoint meter able to support negative pressure, as well as the use of a orifice plate and two vacuum meters (vacuum meters) capable of measuring the pressure of condensable steam as well as a orifice which, allow a pressure drop. The signals on both sides of the orifice plate and the one from the dewpoint temperature are sent to a data acquisition card, which allows to measure, with the help of an algorithm, the amount of water in weight that flows per time unit.

6 Claims, 3 Drawing Sheets

DEVICE TO CONTINUOUSLY DETERMINE THE RATE OF EXTRACTION OF WATER STEAM USED FOR DRYING TRANSFORMERS

FIELD OF THE DISCLOSURE

The present disclosure is related to equipment for the measurement of flow of water steam for optimization of processes of dried of transformers low vacuum, and particularly this relates to a device for determining continuously the rate of extraction of steam water utilized for the dried of transformers.

BACKGROUND OF THE DISCLOSURE

Many transformers and other electrical equipments use cellulose as an insulating element in their manufacture. The dielectric properties of the cellulose along with its abundance, its durability, and the facility in its manipulation during the manufacture processes, they become an element ideal for the manufacturing of electric. It is common to find equipment that use dielectric fluids, moreover the cellulose, as booster of the dielectric capacity of the cellulose, moreover they serve as mean for transfer of heat to the outside, protecting to the equipment of damage due to the exposure to high temperatures of the electric material. Nevertheless, despite of the multiples advantages of this material, it is well known for more than half century that its aging involves to the loss of some of its fundamental properties, among them its dielectric stiffness. Because of this reason, it is fundamental to do all possible to avoid the degradation of this component and to avoid possible problems with the operation of the equipments related to failures of dielectric material.

Power electrical transformers are devices that modify the voltage in the electrical circuits for power transmission, its power is high, so that also, the ability of current conduction is rather high. Due to that the power electric transformer use very high voltages, insulating systems based on cellulose (paper, carton, wood) are used, as well as a dielectric fluid that serves as mean of cooling, it is necessary that the content of humidity be low inside the power electric transformers to avoid to impact in the dielectric properties of these components, not only in the first periods of operation, but along its operating life. These appliances are disarmed in the plant prior to shipment and subsequently armed and reconnected once they arrive to the substation where they will be used. For its reconnection and inspection in the interior, specialized personnel get inside the tank of a power electric transformer, but is required for, security reasons, that a totally open registry be maintained, which favors there has exchange between the atmospheric air and the humidity that this contain, and the water to be placed in the surface of the conductors and its isolations. Once the transformer is inspected and internal connections made and before filling it with dielectric oil for its powering; it is required to remove the moisture in the air and deposited it on the surface of the isolations. For the drying process described above there is a practical and conventional method, which takes place by extracting the air and lowering the pressure inside the tank of the power electric transformer by means of a vacuum pump, but not before ensuring the tightness in the tank. The connection between vacuum pump and the closed tank is carried out by means of a hose or pipeline. Such a process can last several days depending on the humidity that was introduced and size or volume of the tank. There are also tests to determine with certainty the level of humidity of the transformer. Most of these tests are related to the calculation of the pressure inside the tank, since the pressure inside the tank, it is a result of the steam pressure that has the humidity of the interior. Units of measurement of pressure that are commonly used are the millimeters of mercury, with the understanding that the start of the extraction process, the system has an atmospheric pressure that is about 760 mm of mercury at sea level, either an atmosphere.

During installation and start-up of a power transformer, the drying process is one of the activities that takes longer to be completed, moreover from the risks of a reprocessing and dead times that could exist in the determination of the humidity test as validation test to conclude the drying process.

Because of the aforementioned, the monitoring of the efficiency of the process of extraction humidity or drying has a great value. From time to time said monitoring is done by isolating (closing an intermediate valve between the tank of the transformer and the vacuum pump) the tank and measuring as the pressure grows in the same, that is to negative pressure (but without extraction). In this method, the depression (increase of pressure in a closed container) according to the volume of the tank during half an hour. If the increase is significant, then it is likely that an air entry exists at any part of the transformer or that the high pressure of steam is causing that the pressure within the tank increase in a fast form.

There are conventional methods used by most of the installers of power electric transformer to determine the moisture in the transformer and that define the termination of the drying process.

The most used method used to measure moisture content inside the power electric transformer is by injecting air or extra-dry nitrogen, once the vacuum process is cut, it should fall back to levels of 0.5 mm of Hg of pressure.

Subsequently, the air injected is allowed to mix with the moisture remaining on the surface inside the tank for a time of between 12 and 24 hours. Later, the dewpoint temperature is measured (which refers to the temperature to which the moisture contained in a gas starts to condense) in a sample (nitrogen or extra dry air) that is pressuring to the transformer, to determine steam pressure of such gas through adjusted graphics for this measurement (Piper or Oomen charts). A lower dewpoint temperature implies a smaller humidity in the gas. Now, once the value of this variable is obtained (steam pressure), with another table and with the approximate temperature of the isolations and the value of steam pressure, the residual humidity is calculated. This process has the inconvenience of requiring around 1.5 days to calculate the moisture content.

The other process to determine the content of humidity in the power transformers is via the measurement of the flow of water steam that is extracted of the same one, nevertheless the flow that has interests at the end of the process of drying. Conventionally a parameter has been established for maximum flow according to the content of isolations (kilograms of wood, carton and paper) and in this manner, to calculate the humidity in the transformer. To account such water flow, the steam that flows during the extraction is collected via the steam condensation of the same and subsequently the melting of the ice (condensed) for its measurement in a calibrated container. The mechanism to get the humidity is a surface at very low temperatures (below −45° C.), since the quantity of water in the air that flows is extremely low which, makes necessary to utilize cryogenics temperatures and therefore to condense the steam. This system is called cold trap, in some cases it uses carbon dioxide in the form of dry ice and acetone for cooling a surface homogeneously or with liquid nitrogen. The established procedure indicates that the condensate in order to be considered representative, it must have a collection of at least 4 hours of continuous flow.

In either both of the most common methods there are disadvantages involving dead times and, as well as, low repeatability or reproducibility. In the case of the measurement which requires the injection of an extra dry gas, the major constraint is the dead time in which they are incurred from when the gas is injected (which you can be between 2 and 4 hours depending of the size of the unit) moreover the time that should be expected to allow the extra dry air reaches a certain balanced with the moisture of the interior (which regularly requires more than 12 hours). Finally, within these same dead times and once it is within the allowed level of moisture, then starts another vacuum process for filling (taking about 2 to 4 hours). It should be noted that the skill persons recommend to perform this test at temperatures above 10° Celsius and this is because the behavior become rarefy as the temperature lowers, (it is not strange that in the field to reach temperatures lower than 10 Celsius in the transformer during the night), which delays the results for more hours. Therefore, since this is not a measure instrument for continuous measurement, is considering about 24 hours to know the conditions of humidity inside the apparatus and to be able to fill the unit with oil.

In the measurement method with water collection via a cold trap, a main disadvantage is the required preset, because of the very low amounts of water, it is important that the period is at least 4 hours to collect a sufficient amount of moisture, and the other disadvantage is that the cold trap is not regulated, so that the variation in design (it could collect a different quantity of water from the cold surface where water particles contact) in addition that the resulting fluid is a mixture of transformer oil and water (slurry state), which sometimes makes it difficult to measure humidity.

BRIEF DESCRIPTION OF THE DISCLOSURE

A humidity flow meter is provided in the air at negative pressure in the drying of transformers by means of a process of vacuum for extraction of the water, causing a differential of pressure through an orifice plate device and the measurement of drew point continuously. Provided are a pipeline, a continuous dewpoint meter capable to bear negative pressures, as well as the utilization of a orifice plaque and two vacuum meters (vacuum meters) capable to measure the pressure of condensable steams, as well as an orifice plate that allows pressure drop. The pressure signals in both sides of the orifice plate and the dewpoint temperature are sent to data acquisition card which, with the aid of an algorithm, it allows to measure the quantity of water in weight that flows in time unit.

BRIEF DESCRIPTION OF THE DRAWINGS

Objects and features of the present disclosure shall be evident from the following detailed considered description related the attached drawings. However, it is understood that such drawings are only designed as an illustration and not as a restrictive definition of the claimed subject matter. In the drawings, the reference numbers denote similar elements along vary views:

DETAILED DESCRIPTION

The device for continuously measuring the rate of extraction of water steam used in the drying of transformers, in accordance with this disclosure, is an instrument able to assess the flow of moisture in a drying process of power transformers which uses vacuum pumps for the extraction of moisture. Additionally, a method to determine the efficacy and the moment of culmination of the process of drying is described.

Figure 1:
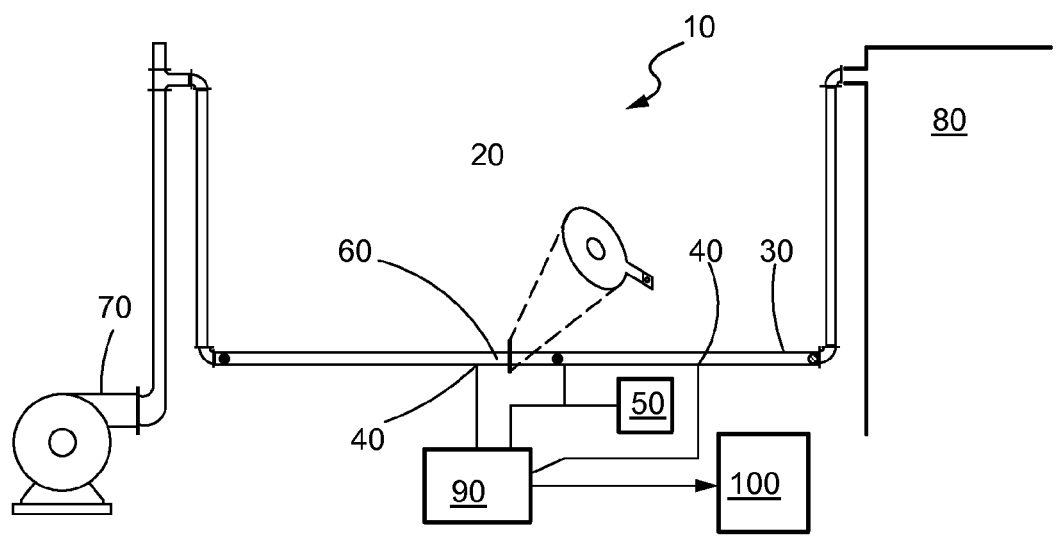
FIG. 1 shows a schematic representation of the device to continuously measure extraction rate of water steam of a tank of a transformer, according to this disclosure.

To this end, referring to FIG. 1, the device (10) to continuously measure the rate of extraction of water steam of a transformer tank, includes: an orifice plate (20) mounted between two flanges inside a pipeline (30); two pressure gauges (40), each one of which is on the side of the orifice plate (20), to measure the pressure drop in the orifice plate; a dewpoint meter (50) inside the pipeline (30); and a temperature gauge (60) inside the pipeline (30), where the device is connected in series between a vacuum pump (70) and the transformer tank (80).

The signals obtained from the meters of the device, pressures, temperature and dewpoint are used to determine the extraction speed of steam water of the transformer tank.

The evaluated magnitudes for these elements are used to quantify the extraction rate of the water performed by the vacuum pump.

Figure 2:
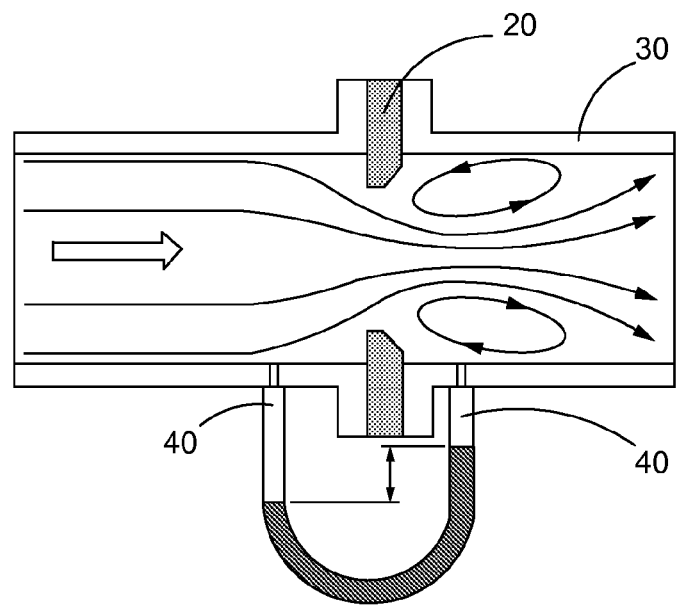
FIG. 2 is a representation of the lines of flow of the fluids crossing through a orifice plate, which they change of path and they cause differential of pressure.

Referring to FIG. 2, the flow meter is manufactured from a metal pipeline section (30) with flanges and accessories for instrument connections. An orifice plate is installed at the middle of two flanges so when they are crossed by the flow generated by the suction of vacuum pump, and because it is a smaller cross section area, there is a pressure drop whose magnitude is determinate by the use of pressure meters (40) placed on both sides of plate (20).

The orifice plate (20) is a metal sheet that has been drilled an orifice of known diameter. On the same section of the pipeline, a dewpoint meter and temperature sensor are placed, the elements of these instruments will be in direct contact with the flow that goes through the pipeline is in the drying process. The signals of pressure, temperature and dewpoint are transmitted via a data acquisition card (90) to a computing device (100) (elements shown in FIG. 1) which, use it as parameters for evaluating the extraction rate of water of the process, by using mathematical functions derived from principles of fluid mechanics and thermodynamics (equations of flow measurement in vacuum conditions for laminar, critic and molecular regimes).

Particularly, the volume per second is equal to the product of the conductance by the drop (difference) of pressure:

Flow:

$$Q_{mol} = C_{mol}(p_1 - p_2) \text{ [Pa m}^3\text{/s]}$$

Conductance:

$$C_{mol} = \frac{d^3}{L}\left[\frac{\pi g_c RT}{18(pm)}\right]^{1/2}$$

Air @ 20° C., $$C_{mol} = 121.3 \frac{d^3}{L}$$

For any case the mass flow (m, gr/seg):
m=Q (pm)/R T
(pm)=average weight of the gas (g/mol)
R=C.onstant of the Ideal gases=0.082 lt atm/° K.mol
T=temperature of the system IK)
Q=Flow (atm lt/seg)

The calculations are performed automatically in computational device, the computational device includes a screen to show the information delivered by the sensors and the results that are produced upon evaluating the mentioned mathematic functions; this computational device also includes the necessary elements for electronic storage of the measurements performed and other relevant data such as date, hour and the accumulated flow.

The instrument should be connected in series with the pipeline or hose that is connected to the transformer tank or to the power unit that is being processed and the vacuum pump, using the appropriated accessories for such purposes and assuring that there are not leaks, because ashes will pollute the results of the measuring.

The procedure to calculate the speed of water removal water of transformer tank is presented. The calculation procedure to calculate the speed of water removal comprises the following steps:

1) to record the change in the vacuum pressure in a given period of time (e.g. 1 hr);
2) to determine the mass flow (lb/hr) based on data curve obtained with Piccolo data for the used pump;
3) to multiply the mass flow obtained in the time determined in step (1), in order to obtain the air mass (pounds, or grams) that flow in that period;
4) to calculate partial pressure of water steam, considering that partial pressure of water is equal to the steam pressure and dewpoint temperature, $P_{H2O}=P°_{H2O}$ @ $T_{dew}$; and using the following equation (obtained by lineal regression according to the reported data as in the "Handbook of Chemistry and Physics", 1994; CRC, $R^2=0.9925$):

$P_{H2O}=6005.7 \exp(0.1065\ T_{dew})$,
wherein:
$P_{H2O}$=partial water pressure (microns of Hg)
$T_{dew}$=Dewpoint temperature (° C.);

5) to calculate the water moles fraction in the gas phase ($y_{H2O}$) such as $y_{H2O}=P_{H2O}/P_T$
wherein:
$y_{H2O}$=Fraction of water moles (dimensionless)
$P_{H2O}$=Partial water pressure (microns of Hg)
$P_T$=Total pressure of the system (microns de Hg);

6) with the water moles fraction gas phase ($y_{H2O}$) obtained in the step (4), obtain the mass fraction by multiplying the respective molecular masses;
7) to multiply the mass fraction of water by the mass of humid air, in order to obtain is mass of extracted water;
8) to divide the water mass by the time to obtain the removal speed,
9) to draw water removal speed vs. time for drying operation;
10) the drying process can be terminated when water removal speed is minor to 39/h per mega gram of weight of isolation (ANSI/IEEE C57.12.12-1980 Standard).

Example Prior Procedure
1) $\Delta t$=1 h; P=54 microns Hg; $T_{dew}$=-61.0° C.; T=25.8° C.
2) using the equation of a pump 3726:
P=33.673 m+8.7314
m=(P-8.7314)/33.673
wherein: P=pressure in microns
m=mass flow in lb/hr
m=(54-8.73141/33.073
m=1.3443 lb of moist air
3) 1.3443 lb/hr=610.34 g of moist air/hr
4) $P_{H2O}$=6005.7 exp(0.1065 $T_{dew}$)
=$P_{H2O}$=6005.7 exp(0.1065*(-61.0))
$P_{H2O}$=9.061 microns
5) $y_{H2O}=P_{H2O}/P_T$=9.061/54=0.1678 moles of water/mol of moist air
6) 0.1678 moles of water (18 g/mol)=3.0203 g of water if in one mole of mixture there are 0.1678 moles of water, then in a mixture mole will have: (1-0.1678) moles of air=moles of air*[(0.8)28)+(0.2)(32)]g/mol=23.9673 g of air 3.0203 g of water/[3.0203 g water+23.9673 g air)=0.1119 g water/g moist air
7) 610.339 g of moist air/hr*0.1119 g of water/g of moist air=68.2969 g of water/hr.

The moist air flow is determined by a difference of pressure caused by an orifice plate.

Figure 3:
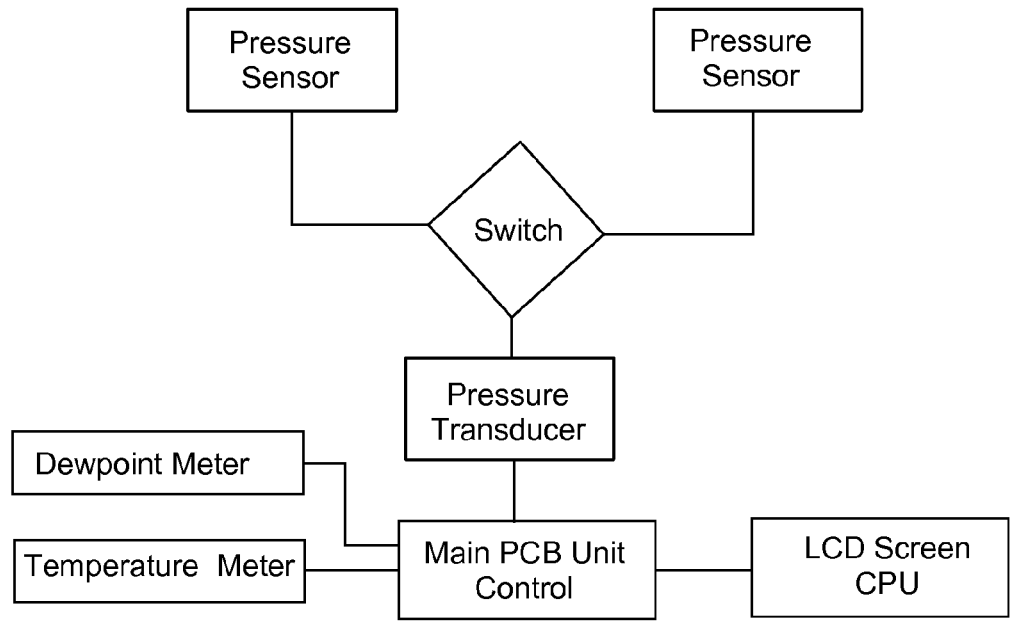
FIG. 3 represents a block diagram of the signals used in the device, according to this disclosure.

The system of mass flow measurement integrates 3 different types of sensors (dewpoint, pressure and temperature). In the FIG. 3 depicts a block diagram of signals used in the equipments.

Figure 4:
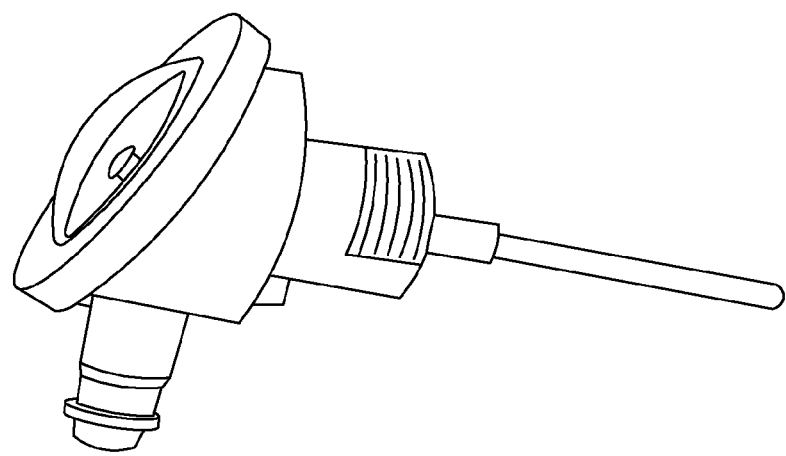
FIG. 4 is a graphic representation of a temperature sensor of the device according to this disclosure.

Temperature sensor: the temperature sensor selected is type RTD. In particular, a sensor type PT1000 was chosen to disregard the effects of contact resistances that may appear in the connections. The sensor will be protected by a Nema 4x enclosure of stainless steel, with no polarity and its mechanical assembly will be type NPT ½. The contacts are protected by a Nema 4 instrumentation box. The temperature sensor is shown in FIG. 4.

Figure 5:
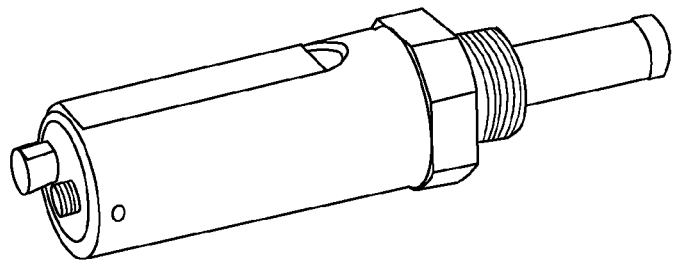
FIG. 5 show a dewpoint transmitter, used by the device according to this disclosure.

Referring to FIG. 5, the dewpoint transmitter is shown, which must operate in the range of +20 to -80° C. with an accuracy of +/-2° C. It should be protected in an enclosure Nema 4x of stainless steel, mechanical assembly type NET ½" and its output must be linear in the range of 0-10 VDC. The power supply will be 24 VDC. The transmitter selected is a DMT-152 model from Vaisala and part number DMT152-B1CB210A330A1X.

Figure 6:
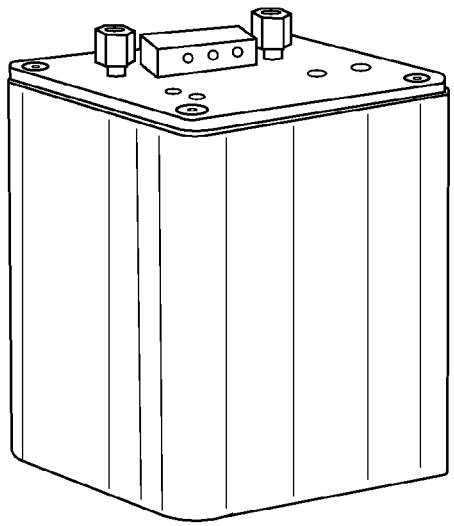
FIG. 6 show a pressure transducer used by the device according to this disclosure.

The pressure transducer of should operate in the range from 0.001 to 1 Torr. Its function will be to translate the variations produced in a bulb (sensor element) of the type thermocouple suitable for the required measurement range. The power supply is 24 VDC and its enclosure made of aluminum. It should provide an analog output in the range of 0-1 VDC proportional to pressure reading and an accuracy of at least 10%. The selected transducer is the model DAVE of Hastings. The pressure transducer is shown in FIG. 6.

Figure 7:
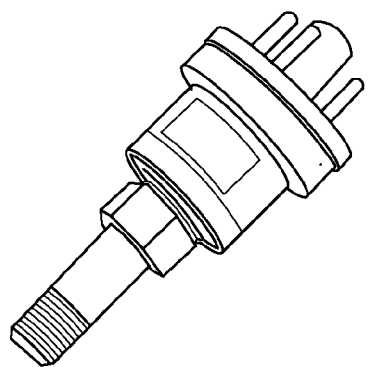
FIG. 7 depicts a pressure bulb of used in the device according to this disclosure.

The pressure bulb should be of thermocouple type, and will be protected in a heavy duty enclosure of stainless steel with mechanical connection type ⅛" NPT. This sensor must be compatible with the pressure transducer selected and be appropriate for the range of 0.001 to 1 Ton. The pressure bulb used will be the model DV6 of Hastings. The pressure bulb is shown in FIG. 7.

The description of the data acquisition card and the computer is out of the scope of this disclosure, it will be apparent to those skilled in the art that a number of variations and modifications can be done without departing from the scope of the claims.

An example of the calculation flow of moisture, described in grams of $H_2O$ per hour, is shown, for the device to continuously measure the rate steam water extraction used in the drying of transformers in accordance with this disclosure.

EXAMPLE

In order to not depend on the sensitivity of the instrument (in this case, a data acquisition card) and to obtain a comparable measure using an orifice plate and a pipeline in molecular regime, a plate with the same conductance in this regime is calculated, namely:

Molecular conductance of a pipeline with 4" in diameter and 5 meters in length:

$$C_{molecular\ pipeline} = 12.1\ (d^3/L) = 12.1((1.16)^3/500) = 25.38\ [l/s] \quad (1)$$

For the orifice plate, it has:

$$C_{molecular\ orifice} = 2.68\ d^2\ \sqrt{(T/pm)} = 9.25\ d^2\ [l/s];$$

where pm=0.028 kg/mol
T=293° K.
d=10.16 cm

Para $C_{molecular\ pipeline} = C_{molecular\ orifice}$ $$d = (25.38/9.25)^{1/2} = 1.66\ cm \quad (2)$$

For an orifice of diameter d=1.66 cm, it has the same molecular conductance than a pipe 4" diameter and 5 m long.

It is well known that:
if Pd>0.8 Pam=>laminar flow;
if Pd<0.01 Pam=>molecular flow;
0.01<Pd<0.8 Pam=>flow slider.

For a pipe of 4" diameter and operating at pressures≈80 N
Pd=(80/7.5)*0.1016=1.087=>then molecular flow is negligible.

The orifice of plate used is of 1.67 cm in diameter. To determine the flow should be aware that during the process $P_{waters\ up} \geq 2$ ($press_{waters\ down}$). This status $2P_2$ determines an orifice of critical flow.

In the critical flow condition, the mass flow is given by (Levenspiel)

$$G_{nz}^* = p_{water\ up}\left[\frac{K(Pm)}{RT_o}\left(\frac{2}{1+K}\right)^{\frac{(K+1)}{(K-1)}}\right]^{1/2}\ [Kg/m^2s] \quad (3)$$

wherein
Pm=28.99 mol$^{-1}$
R=8.31 Pa mol$^{-1}$ K$^{-1}$
T$_0$=298 ° K.
K=1.4 (diatomic gases)
The flow through the orifice will be $$Q = G_{nz}^* A = \frac{\pi}{4}d^2(G_{nz}^*)\ [Kg/s] \quad (4)$$

wherein d=orifice diameter, in meters.

In a pipeline with 4" diameter with an orifice plate of 1.67 cm in diameter, a pressure of P2=36 microns Hg=4.8 Pa, a pressure P$_1$=114 microns Hg=15.2 Pa, a dewpoint of −52.71° C.=304.59° K., D=10.16 cm, d=1.67 cm.

As P$_1$>2P$_2$ is considered as critical flow (Levenspiel).
Steam pressure:

$$P_v = \frac{6005.669\ e^{(0.1065(-52.71))}}{7.5} = 2.92\ Pa$$

Mass Flow
Using (3):

$$G_{nz}^* = 15.2\left[\frac{1.4(0.0289(0.81)+0.018(0.19))}{8.31(304.59)}\left(\frac{2}{2.4}\right)^{\frac{2.4}{0.4}}\right]^{1/2} = 0.033\ kg/m^2s$$

Q=26.4[g/h] this is the moist air flux.

$$Q_{H2O} = \left[\frac{26.4\ g}{h}\left(\frac{1\ mol}{26.8\ g(wetair)}\right)\left(\frac{180(0.19\ g)}{mol(water)}\right)\right] = 3.37\ [g_{H2O}/h]$$

The novelty is the orifice plate in the steam flow meter, during the drying under vacuum of transformer. To determine the flow in any of the regimens (laminar, intermediate, molecular) is required to measure a pressure differential and not only one of the pressures. Now, if an orifice plate is not available, a rigid steel pipe can be used, place the pressure meters at a distance of 5 mm separation at least, since this distance allows a pressure drop sufficiently large to allow establishing a correct calculation including the accuracy of the equipment used.

Additionally, because the maximum moisture content is related to the tons of insulation that the power transformer could contain, the computational system has the ability to automatically measure the amount of insulation from two variables, voltage and capacity, using a regression algorithm that gives an accurate assessment of the amount of insulation and which is statistically validated. The amount of isolation is related to, among other aspects of voltage and as it increases, it requires a design with greater thickness of insulation for the conductors and thus, to fulfill a safe operation condition. In the case of the capacity, that is also a data from the plate that all the transformers should report, is a critical variable because to a greater capacity, the conductor of the transformer is greater and the diameter of the same one enlarges, that results in an increase of the isolation content upon as the perimeter increases. Aforementioned allows to the installer and to the responsible for quality assurance in the drying process, to determine in accurate and easy manner with the plate data, the quantity of isolation, moreover that estimation is accurate.

Because a critical element in this process is the assurance of a proper tightness, a precise measurement of the dewpoint meter, as well as for the capacity of pump suction, another additional novel element already aforementioned, it is an initial diagnosis that the system performs in order to identify certain deviations in the parameters in the equipment configuration prior to the drying process. The equipment is capable of identifying a failure in the tightness of the device, hoses (pipeline), flanges and any connection that can be found just before the valve that isolates the tank or transformer, this is achieved through the detection of a high value in the flow once the mentioned valve is closed. That is, the volume is so low compared with the whole tank that a continuous flow should not exist because this indicates a deficient tightness. Within the self-diagnosis the device also has the function to identify deficiencies in the pump (suction defect), since the equipment will report a high pressure after closing the valve that isolate the tank and system.

Finally, if there is a deviation in the measurement of the dewpoint, the system will display an alert message telling that a revision of the bulb and connections of the meter is required. Again, the way this deviation is determined (high temperature of the dewpoint) it is because a very low level steam content must exist after closing the isolating valve, but having proper tightness and suction, that is, once the pump starts, the steam and air molecules will tend to travel to the pump in a very short time and the value measured by the meter of dewpoint will continuously decrease to near the final values, therefore if this does not happen early, this is indicative of a fault in the sensor. The advantage of this auto diagnostics is that major rework is avoided since any deviation in the suction and/or tightness of hoses and fittings is early identified.

The instrument will show the user at all time, the water flow rate and it will inform via a message that the process has been successfully finished.

The system operator must set it before use it with information regarding the purpose of drying apparatus which can be:
  Operation tensions
  Operation power The scope of the measurement is for gas temperatures greater than 10° C., due to the fact that for temperatures under the one mentioned, the extraction is very poor, since it depends on the diffusion of the humidity that, at the same time, depends more on the temperature than the low pressure. This is, as long as the gas temperature descends under the 10° C., the quantity of extracted water is critically descending, but not this not a correct way to determine the condition of acceptable humidity in the transformer, but the water that is found in the surface of the isolations will not extracted to the required flow, therefore a perceived sensation of dryness condition in the equipment would be perceived.

One way to assess the performance of this equipment was via the comparison of this system in drying processes for power units with both systems, the mentioned on with a continuous and a cold trap whose surface and geometry allow to reduce any error if the molecules do not collide with the surface such as if were a coil. The content of water collected by cold trap against online measurement had an error of about 5%. The above was done with a sample of 5 units at different temperatures of operation.

The advantages of the system can be expressed in terms of the elimination of activities that do not add value and the reliability of measurement. They are detailed:
  a) Direct, i.e. the mass flow meter for transformers, allows a measurement on a continuous basis from the amount of moisture in relation to the amount of isolation per used algorithm, so, it does not require knowing the contents as a required data.
  b) Real-time measurement, the system requires no extra time to know about the moisture inside, which saves at least 24 hours of set up compared to the method of steam pressure/dewpoint
  c) Accuracy, the algorithm uses two flow regimes, allows calculating according what the pressure levels
  d) High repeatability and reproducibility, the cold trap systems are not standardized so they could have different amounts of water and for mass flow meter only one diameter is considered and from this the measurement is done.
  e) The auto diagnostics allows increasing the reliability of the system, while mitigating the risks of failure of tightness (fault in the pipelines sealing) and/or pollution in the online measurement system of dewpoint since it identifies with opportunity the deviations of this type.
  e) Precision, the air injection method or steam pressure/dewpoint method shows variation as the temperature begins to fall.
  f) Cost reduction, since no dry ice, no heating system, neither graduated containers, in the case of the cold trap, or no bottles nor extra dry cylinders are required. The self-diagnostics acknowledges faults in the air extraction by poor vacuum in the pumps, so reworking costs are reduced.

What is claimed is:

1. A device to continuously measure an extraction rate of water steam from a transformer tank, the device comprising:
  A pump operating at sub-atmospheric pressure;
  a pipeline extending between the vacuum pump and the transformer tank;
  an orifice plate mounted between two flanges inside the pipeline;
  first and second pressure meters, disposed on opposite sides of the orifice plate-and configured to measure a pressure drop across the orifice plate;
  a dewpoint meter operably coupled to an inside of the pipeline; and
  a temperature meter operably coupled to an inside of the pipeline.

2. The device of claim 1, wherein the orifice plate, the first and second pressure meters, the dewpoint meter, and the temperature meter are in direct contact with a fluid flow through the pipeline during a process of drying a transformer.

3. The device of claim 1, wherein the temperature meter comprises a type RTD temperature sensor.

4. The device of claim 1, wherein each pressure meter comprises a thermocouple type pressure bulb disposed inside a heavy duty enclosure of stainless steel with a mechanical connection of type ⅛" NPT.

5. A method of continuously measuring a moisture flow through a pipeline during a vacuum process for drying of power transformers, using a device connected in series between a vacuum pump and a transformer tank; the device including: an orifice plate mounted between two flanges inside the pipeline; first and second pressure meters disposed on opposite sides of the orifice plate and configured to measure a pressure drop across the orifice plate; a dewpoint meter operably coupled to an inside of the pipeline; and a temperature meter operably coupled to an inside of the pipeline, the method comprising:
  determining an air flow expressed in units of mass per time units based on a power of the vacuum pump and the differential pressure caused by the orifice plate;
  determining a partial pressure of a water steam based on a measured dewpoint temperature of the moist air, considering that the partial pressure is equal to a steam pressure to the dewpoint temperature;
  determining a mole fraction of water in gas phase (yH20) by dividing the partial pressure of the water steam and a total pressure within the pipeline;
  determining a mass fraction by multiplying by respective molecular masses; and
  multiplying the mass fraction of water by a moist air flow, in order to obtain a speed of water removal.

6. The method of claim 5, wherein the vacuum process for drying is complete when a speed of water removal is less than 3 g/h by mega gram in weight of the insulation.

* * * * *